(12) United States Patent
Sater (10) Patent No.: US 7,303,574 B2
(45) Date of Patent: Dec. 4, 2007

(54) OCCLUSION CATHETER WITH FRICTIONAL VALVE

(75) Inventor: Ghaleb A. Sater, Lynnfield, MA (US)

(73) Assignee: Medtronic Vasculor, Inc., Santa Rose, CA (US)

( * ) Notice: Subject to any disclaimer, the term of this patent is extended or adjusted under 35 U.S.C. 154(b) by 698 days.

(21) Appl. No.: 10/636,830

(22) Filed: Aug. 7, 2003

(65) Prior Publication Data

US 2005/0033346 A1 Feb. 10, 2005

(51) Int. Cl.
*A61M 29/00* (2006.01)
(52) U.S. Cl. ..................... 606/194; 604/99.02
(58) Field of Classification Search ............. 604/99.02, 604/99.04, 96.01–103.04; 606/191, 192, 606/194, 195
See application file for complete search history.

(56) References Cited

U.S. PATENT DOCUMENTS

| | | | |
|---|---|---|---|
| 5,059,176 A * | 10/1991 | Winters ................... | 604/99.04 |
| 5,520,645 A | 5/1996 | Imran et al. | |
| 5,683,410 A | 11/1997 | Samson | |
| 6,050,972 A * | 4/2000 | Zadno-Azizi et al. .... | 604/97.01 |
| 6,090,083 A | 7/2000 | Sell et al. | |
| 6,096,055 A | 8/2000 | Samson | |
| 6,102,891 A | 8/2000 | Van Erp et al. | |
| 6,231,588 B1 * | 5/2001 | Zadno-Azizi ............... | 606/200 |
| 6,325,778 B1 | 12/2001 | Zadno-Azizi et al. | |
| 6,355,014 B1 | 3/2002 | Zadno-Azizi et al. | |
| 6,440,097 B1 | 8/2002 | Kupiecki | |
| 6,475,185 B1 | 11/2002 | Rauker et al. | |
| 6,500,147 B2 | 12/2002 | Omaleki et al. | |
| 6,500,166 B1 | 12/2002 | Zadno Azizi et al. | |
| 6,544,276 B1 | 4/2003 | Zadno-Azizi et al. | |
| 6,743,208 B1 * | 6/2004 | Coyle ..................... | 604/164.13 |
| 2002/0010488 A1 * | 1/2002 | Crawford et al. ........... | 606/194 |
| 2002/0133117 A1 | 9/2002 | Zadno-Azizi et al. | |
| 2003/0004461 A1 | 1/2003 | Kupiecki | |
| 2003/0055398 A1 | 3/2003 | Imran | |

* cited by examiner

*Primary Examiner*—Anhtuan T. Nguyen
*Assistant Examiner*—Elizabeth Houston (57) ABSTRACT

A system for treating a vascular condition, including a hollow guidewire having a central lumen and an inflation hole formed in a sidewall of the hollow guidewire, an occlusion balloon attached proximate to a distal end of the hollow guidewire, and a frictional valve. The frictional valve includes a portion of a core wire positioned within a proximal end of the hollow guidewire, a valve plug attached to the core wire, and at least one frictional plug attached to the core wire proximal to the valve plug. Flow of fluid through the central lumen of the hollow guidewire is controlled by axial translation of the core wire to position the valve plug with respect to the inflation hole, while the frictional plug provides a tailored valve compliance characteristic.

14 Claims, 10 Drawing Sheets

OCCLUSION CATHETER WITH FRICTIONAL VALVE

FIELD OF THE INVENTION

This invention relates generally to balloon catheters and guidewire deployment of catheter-based treatment tools. More specifically, the invention relates to an occlusion catheter with a frictional valve mechanism.

BACKGROUND OF THE INVENTION

The successful implementation of balloon-catheter procedures involves controlling the flow of fluid to a balloon of a catheter or a treatment area in a vessel of a human body. Medical balloon catheters have been proven efficacious in treating a wide variety of blood vessel disorders such as intravascular restrictions due to atherosclerosis or restenosis. Balloon angioplasty, or percutaneous transluminal coronary angioplasty (PTCA), is commonly used to alleviate stenotic lesions in blood vessels, thereby reducing the need for heart bypass operations.

Balloon catheter and guidewire-deployed treatment systems are used to temporarily occlude a vessel in the coronary vasculature during diagnostic and interventional procedures. Guidewires help guide the insertion of catheters and various medical instruments to a desired treatment location within the vasculature of a human body. A flexible guidewire can be advanced through the blood vessels until the guidewire extends across the vessel segment to be treated. Treatment catheters, such as a balloon dilation catheter for PTCA, may be inserted over the guidewire and similarly advanced through the vasculature until they reach the treatment site.

Areas of vascular stenoses or occlusions in a vessel are often characterized by having a mineral component. A variety of different procedures has been developed for treating vascular diseases with these calcified areas. Some treatment methodologies involve the mechanical removal of the blockage, mechanical debridement, atherectomy, balloon angioplasty, stenting, or bypass surgery procedures.

Intravascular procedures often use one or more catheters, such as balloon catheters to dilate vascular restrictions or atherectomy catheters to remove the restriction. Unfortunately, the intravascular procedures associated with these devices may result in particles being dislodged while the restriction is dilated or cut. Such dislodged particles may move downstream from the area of restriction, possibly causing an embolism, which could compromise the flow of blood to the surrounding tissue.

Treatment procedures employing occlusion balloon catheters and aspiration catheters have been developed to help prevent potentially embolic debris from migrating with the blood stream. The occlusion balloon catheter blocks or impedes blood flow while the aspiration catheter aspirates and removes embolic particles from the area of the stenosis.

In one exemplary method for reducing embolization, the treatment area is continuously aspirated while the aspiration catheter is moved, as described in "Methods for Reducing Distal Embolization," Imran, U.S. Patent Application 2003/0055398 published Mar. 20, 2003. This method is proposed to prevent embolization of any particles that may be created during the crossing of the intravascular inclusions. An adapter for controlling fluid flow in an exemplary angioplasty balloon catheter is described in "Low Profile Angioplasty Catheter and/or Guide Wire and Method," Imran et al., U.S. Pat. No. 5,520,645 issued May 28, 1996. The balloon-on-a-wire catheter has a flexible elongate tubular member with proximal and distal extremities and with a lumen extending from the proximal extremity to the distal extremity. A removable inflation fitting is secured to the proximal extremity of the flexible elongate tubular member for supplying an inflation fluid to the lumen for inflating and deflating the balloon. Fluid flow may be controlled with a removable inflation means such as a conventional Tuohy Borst adapter having a tubular member formed of suitable material such as a clear plastic. For example, a Tuohy Borst adapter can provide a temporary fluid or airtight seal with the compression of a silicone ferrule.

During treatment procedures using catheters, it is not uncommon for multiple catheters to be introduced and removed sequentially over a guidewire, the latter acting as a guide for the exchange of one treatment catheter for another. Embolic containment procedures typically employ one or two occlusion balloons in conjunction with an aspiration catheter. One example of an inflatable occlusion catheter includes an occlusion balloon mounted distally on an elongated wire-like shaft that extends through a guidewire lumen of a primary dilation or atherectomy catheter. The balloon is advanced through a vessel, positioned distal to the site of the stenosis, and temporarily inflated to prevent embolic particles from migrating downstream as the occlusive restriction is being dilated or cut. After the restriction has been treated, the primary treatment catheter can be removed from over the guidewire of the occlusion balloon catheter. An aspiration catheter can then be advanced to the treatment site to aspirate any embolic debris generated during the treatment. Once the embolic particles have been aspirated, the occlusion balloon(s) is/are deflated and removed from the patient.

An occlusion catheter is often constructed as a guidewire having a hollow shaft, a flexible, shapeable distal tip, and a deflated elastomeric occlusion balloon attached at the proximal end of the distal tip. During use, the distal tip of the guidewire and the balloon cross the lesion, an inflation device is attached to the proximal end of the catheter, and the occlusion balloon is inflated with dilute contrast agent. Following the inflation of the balloon, an angiogram using fluoroscopy may be taken to ensure complete occlusion by the balloon.

The occlusion guidewire can be used in coordination with other treatment catheters to infuse or deliver fluoroscopic material and therapeutic agents to the treatment site. With the occlusion balloon inflated, balloon angioplasty or stenting may be performed. A handheld inflation device can be removed from the proximal end of the catheter while the occlusion balloon remains inflated, and then a stent-delivery catheter may be exchanged to provide a percutaneous transluminal angioplasty. The embolic particles that are released during a coronary angioplasty or stenting procedure may remain upstream of the inflated occlusion balloon. Following the removal of the angioplasty balloon catheter or stent-delivery catheter, an aspiration catheter may be introduced over the occlusion guidewire to aspirate the particles.

An exemplary occlusion catheter is described by Rauker and others in "Occlusion Device," U.S. Pat. No. 6,475,185 issued Nov. 5, 2002. The occlusion device includes an elongated tubular shaft having an inflatable balloon disposed near the distal end of the elongate shaft with a proximal seal of a sufficiently small profile to allow a second catheter to pass over the distal occlusion device while the inflatable balloon remains uninflated. One occlusion device includes an elongated fluid displacement rod within the elongated shaft of the occlusion device, providing both a fluid pressure source and a seal.

The flexibility of the catheter as well as the guidewire is important for advancing medical devices over the guidewire. Omaleki and others suggest improvements to the properties of the catheter and the wire on which the balloon is attached, as disclosed in "Flexible Catheter," U.S. Pat. No. 6,500,147 issued Dec. 31, 2002. In an embodiment of the invention, connecting wires extend through the balloon from the distal end of a catheter body to the proximal end of a core wire. The core wire extends distally away from the connecting wires and the catheter body, having a proximal end extending within the balloon into the catheter tubular body but not mounted therein. The balloon is mounted over a tubular body that is configured to give the catheter longitudinal flexibility.

Controlling the flow of inflation fluid through a catheter is critical to the successful use of balloon catheters. Current occlusion balloon catheters are able to control the flow of inflation and contrast fluid with sealing members such as plugs or valves located at the proximal end of the catheter. An exemplary catheter valve is a plug consisting of a wire that is shaped to provide a friction fit within a hollow guidewire or hypotube, the plug also having a sealing member on the distal end of the wire. The valve is operated by pushing the plug in and out of the catheter shaft, thus moving the sealing member with respect to an inflation hole in the side of the shaft. A valve adapter, or actuator, may be removably mounted on the proximal end of the catheter to control valve operation. The adapter grips the catheter shaft and the plug via frictional pads, which may be moved in conjunction with an adapter knob. An inflation fluid port on the adapter is positioned to line up, or at least fluidly communicate, with the inflation hole in the catheter shaft, providing a continuous fluid path to inflate the occlusion balloon. Fluid is transferred through the hypotube to fill the occlusion balloon.

Several types of sealing mechanisms have been developed to control the flow and seal inflation fluid into the occlusion balloon. Sell and others have used a valve of an inner tube that is closely fit into an outer tube, as disclosed in "Low Profile Valve and Balloon Catheter," U.S. Pat. No. 6,090,083 issued Jul. 18, 2000. The low-profile inflation valve includes a first thermoplastic tube with at least one region of decreased inner diameter, and a structure, which may be a tube, movably located inside the lumen. The region of decreased inner diameter of the first tube forms a seal with a portion of the structure.

A catheter with a valve on the distal end of the catheter is disclosed in "Single-Lumen Balloon Catheter having a Directional Valve," Samson, U.S. Pat. No. 5,683,410 issued Nov. 4, 1997. The valve is operated by a control wire having a valve plug disposed on the wire. The valve seat may be engaged by the valve plug from either direction, depending on the installation of the control wire. The guidewire with its integral valve plug may traverse the body of the balloon to engage the valve seat in the distal end of the catheter. Pushing on the control wire will seat the valve, allowing the introduction of fluid through the catheter lumen to inflate the balloon. A valve used with a related catheter is described in "Single-Lumen Balloon Catheter having a Directional Valve," Samson, U.S. Pat. No. 6,096,055 issued Aug. 1, 2000. This single-lumen balloon catheter assembly has a valve portion extending distal of a balloon portion. A valve plug engages the surface of the valve at the proximal end of the valve, which has a smaller inner diameter than the distal end of the valve. The proximal and distal surfaces of the valve are adapted to engage the plug to form a seal therewith.

A number of improvements to a balloon occlusion catheter and its valve mechanism are proposed in "Low Profile Catheter Valve and Inflation Adaptor," Zadno-Azizi et al., U.S. Patent Application 2002/0133117 published Sep. 19, 2002; "Exchange Method for Emboli Containment," Zadno-Azizi et al., U.S. Pat. No. 6,544,276 issued Apr. 8, 2003; "Method of Emboli Protection using a Low Profile Catheter," Zadno-Azizi et al., U.S. Pat. No. 6,500,166 granted Dec. 31, 2002; "Low Profile Catheter Valve," Zadno-Azizi et al., U.S. Pat. No. 6,355,014, granted Mar. 12, 2002; "Low Profile Catheter for Angioplasty and Occlusion," Zadno-Azizi, U.S. Pat. No. 6,231,588 issued May 15, 2001; and in "Guidewire Inflation System," Zadno-Azizi et al., U.S. Pat. No. 6,050,972 granted Apr. 18, 2000. The catheter includes a low-profile catheter valve with a movable sealer portion positioned within the inflation lumen of a catheter. The sealer portion forms a fluid tight seal with the inflation lumen by firmly contacting the entire circumference of a section of the inflation lumen. The sealer portion is positioned proximate to a side-access inflation port on the catheter, establishing an unrestricted fluid pathway between the inflation port and an inflatable balloon on the distal end of the catheter. The sealer portion can be moved to a position distal of the inflation port, thereby preventing fluid from being introduced into or withdrawn from the balloon via the inflation port. An inflation adaptor can be used for moving the sealer portion within the catheter to establish or close the fluid pathway between the inflation port and the inflatable balloon. In one of the embodiments of the catheter valve, a tubular sealing member is used as a valve mechanism at the distal end of the catheter. The tubular sealer fits tightly within the lumen of the catheter and may rotate within the lumen. Fluid flows through the valve when the tubular sealer rotates within the lumen to align its opening or port to the side-port access of the lumen. The movable sealer for a low-profile catheter is described specifically in "Low profile catheter valve and inflation adaptor," Zadno-Azizi et al., U.S. Pat. No. 6,325,778 issued Dec. 4, 2001.

Another example of a valved balloon catheter having a wire with a valve plug slidably disposed within the inflation lumen is described in "Balloon Catheter with Delivery Side Holes," Kupiecki, U.S. Patent Application 2003/0004461 published Jan. 2, 2003. The valve plug forms an adjustable pressure seal at a valve seat on the distal end of the catheter and allows fluid within the inflation lumen to be pressurized by a fluid source in order to facilitate balloon inflation.

Preferred characteristics of a controllable closing device or valve are discussed in "Balloon Catheter with Valve," Maria van Erp et al., U.S. Pat. No. 6,102,891 issued Aug. 15, 2000. The valve is arranged inside the inflation lumen so that it can selectively close off the lumen. The valve is described as a device controlled by means of pressure or a mechanical connection such as a ball valve, a snap connection, or a membrane having cuts that move apart when a certain threshold value of pressure is reached. The closing device may have two components, whereby the functioning of the valve depends on the positions of the components in relation to one another. Preferably, a portion of the tubular basic body forms one of the valve components, while the other valve component is a second body placed inside the lumen of the tubular basic body, which closes off the lumen or the opening in different axial or radial positions. The components are preferably movable in relation to one another in a rectilinear or rotary direction. Another embodiment of the invention has a one-way valve in the shape of a membrane comprising cuts or a tilting plate inside the lumen placed at a certain angle.

Not only have valves been used to control the flow of inflation fluids to a catheter balloon, but a valve with a sealing member also has been used with a catheter that delivers therapeutic or diagnostic agents through a one or more delivery ports, as disclosed in "Balloon Catheter with Delivery Side Holes," Kupiecki, U.S. Pat. No. 6,440,097 issued Aug. 27, 2002. In one variation of the catheter, pressurized fluid flows from the proximal end to the distal end of the lumen of the catheter and into an inflatable balloon. Also extending from the proximal end to the distal end, a guidewire inside the lumen may have a valve plug disposed on its distal end for selectively seating against a valve seat at the distal end of the catheter to seal the lumen for balloon inflations.

Catheter manufacturers continue to work on developing valve systems that provide more control over fluid flow to and from an occlusion balloon positioned within a vessel in a body. The desirable valve component has a reliable sealing member with rapid positioning capability into an open or closed position, with minimal constriction of fluid transport through the valve to allow rapid inflation and deflation of the occlusion balloon. Therefore, an improved valve for a balloon catheter system is desirable for catheter-employed treatments for vessels in the body, providing greater control of fluid through a catheter, and increasing utility and performance of associated medical devices used during the treatment of vascular conditions.

SUMMARY OF THE INVENTION

One aspect of the invention provides a system for treating a vascular condition, including a hollow guidewire, an occlusion balloon attached proximate to a distal end of the hollow guidewire, and a frictional valve. The hollow guidewire has a central lumen and an inflation hole formed in a sidewall of the hollow guidewire. The frictional valve includes a portion of a core wire positioned within a proximal end of the hollow guidewire, a valve plug attached to the core wire, and at least one frictional plug attached to the core wire proximal to the valve plug. Flow of fluid through the central lumen of the hollow guidewire is controlled by axial translation of the core wire to position the valve plug with respect to the inflation hole, while the frictional plug provides a tailored valve compliance characteristic.

Another aspect of the invention is a frictional valve for an occlusion catheter. The frictional valve includes a hollow guidewire with a central lumen and an inflation hole formed in a sidewall of the hollow guidewire, a portion of a core wire positioned within a proximal end of the hollow guidewire, a valve plug attached to the core wire, and at least one frictional plug attached to the core wire proximal to the valve plug. Flow of fluid through the central lumen of the hollow guidewire is controlled by axial translation of the core wire to position the valve plug with respect to the inflation hole. The frictional plugs provide a tailored valve compliance characteristic.

Another aspect of the invention is a method of treating a vascular condition, including the steps of axially translating a core wire within a central lumen of a hollow guidewire, positioning a valve plug relative to an inflation hole formed in the hollow guidewire, and centering the core wire within the hollow guidewire during the axial translation with at least one frictional plug attached to the core wire at a position proximal to the valve plug.

Another aspect of the invention is a system for treating a vascular condition, including a hollow guidewire with a central lumen and at least one longitudinally oriented slot formed in a sidewall of the hollow guidewire, an occlusion balloon attached proximate to a distal end of the hollow guidewire, and a frictional valve having a portion of a core wire positioned within a proximal end of the hollow guidewire and a frictional plug attached to the core wire. Axial translation of the core wire controls the flow of fluid through the longitudinally oriented slot and the central lumen of the hollow guidewire by positioning the frictional plug with respect to the longitudinally oriented slot. The frictional plug and the longitudinally oriented slot cooperate to provide a tailored valve compliance characteristic.

Another aspect of the invention is a frictional valve for an occlusion catheter, including a hollow guidewire with a central lumen and at least one longitudinally oriented slot formed in a sidewall of the hollow guidewire, a portion of a core wire positioned within a proximal end of the hollow guidewire, and a frictional plug attached to the core wire.

The present invention is illustrated by the accompanying drawings of various embodiments and the detailed description given below. The drawings should not be taken to limit the invention to the specific embodiments, but are for explanation and understanding. The detailed description and drawings are merely illustrative of the invention rather than limiting, the scope of the invention being defined by the appended claims and equivalents thereof. The foregoing aspects and other attendant advantages of the present invention will become more readily appreciated by the detailed description taken in conjunction with the accompanying drawings.

BRIEF DESCRIPTION OF THE DRAWINGS

Various embodiments of the present invention are illustrated by the accompanying figures, wherein.

DETAILED DESCRIPTION OF THE PRESENTLY PREFERRED EMBODIMENTS

Figure 1:
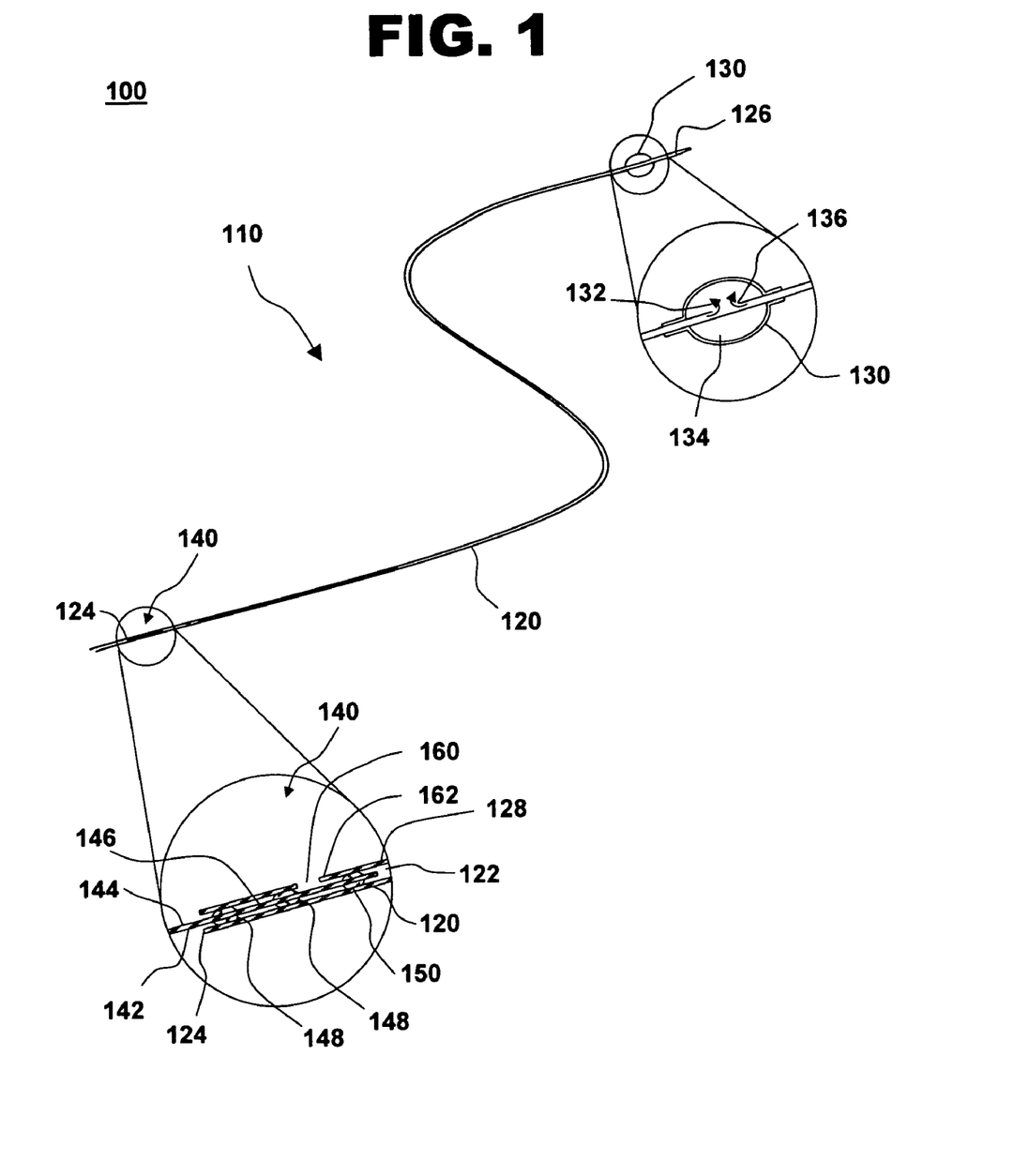
FIG. 1 is an illustration of a system for treating a vascular condition, in accordance with one embodiment of the current invention.

FIG. 1 illustrates a system for treating a vascular condition, in accordance with one embodiment of the present invention at 100. Vascular condition treatment system 100 includes occlusion catheter 110 with hollow guidewire 120 having central lumen 122 and inflation hole 160 formed in sidewall 162 of hollow guidewire 120. Hollow guidewire 120 has proximal end 124 and distal end 126 with occlusion balloon 130 attached proximate to distal end 126. Vascular condition treatment system 100 includes frictional valve 140 with portion 146 of core wire 142 positioned within proximal end 124 of hollow guidewire 120. Valve plug 150 is attached to core wire 142, and at least one frictional plug 148 is attached to core wire 142 proximal to valve plug 150. When deployed, distal end 126 of hollow guidewire 120 is inserted into the body, directed through a vascular path until distal end 126 of hollow guidewire 120 is positioned at the desired location, and occlusion balloon 130 is inflated. Flow of inflation fluid 132 through central lumen 122 of hollow guidewire 120 and into interior region 134 of occlusion balloon 130 is controlled by axial translation or displacement of core wire 142 to position valve plug 150 with respect to inflation hole 160. Frictional plug 148 provides a tailored valve compliance characteristic that results in the desired valve stiffness as core wire 142 and frictional plug 148 move within hollow guidewire 120.

Vascular condition treatment system 100, when inserted into the body, may be used as a temporary occlusion device for blocking fluid flow through arteries or veins. In another medical procedure, vascular condition treatment system 100 is used as a dilation catheter whereby blood vessels with stenoses may be enlarged by inflating occlusion balloon 130 near the blockage. In other applications, vascular condition treatment system 100 is used in coordination with other treatment catheters, such as a stent-delivery catheter, an aspiration catheter, an inspection catheter, a measurement catheter, an angioplasty catheter, an atherectomy catheter, a drug-delivery catheter, an ultrasound device, a measurement device, a laser catheter, an imaging catheter, a treatment catheter or a therapy catheter. Treatment of vascular conditions may include the prevention or correction of various ailments and deficiencies associated with the cardiovascular system, the cerebrovascular system, urogenital systems, biliary conduits, abdominal passageways and other biological vessels within the body.

Occlusion catheter 110 is inserted into the vasculature through a small puncture site at the femoral artery, for example. When positioned, occlusion balloon 130 is inflated, blocking flow through the vessel and temporarily anchoring occlusion balloon 130 to the vascular wall. The long, flexible, small-diameter hollow guidewire 120 may then be used to guide treatment catheters over hollow guidewire 120. In one example, an over-the-wire treatment catheter is delivered. Alternatively, a rapid exchange approach may be used in conjunction with guidewire 120.

Hollow guidewire 120 may be formed, for example, from an extruded or welded tubular material such as nitinol, stainless steel, or other suitable tubing material. In one example, hollow guidewire 120 has an outer diameter of 0.014 inches and an inner diameter on the order of 0.009 inches, with a length between 135 centimeters and 300 centimeters. The length of hollow guidewire 120 may be on the order of 300 centimeters, allowing over-the-wire (OTW) catheters to be inserted into the body once hollow guidewire 120 is in place. In another example, hollow guidewire 120 may be on the order of 175 centimeters in length, suitable for guiding treatment catheters of the rapid-exchange, telescope, multi-exchange and/or zipper types.

At proximal end 124 of hollow guidewire 120, hollow guidewire 120 includes features to aid in the control of inflation fluid 132 through central lumen 122 of hollow guidewire 120. At distal end 126 of hollow guidewire 120, hollow guidewire 120 includes one or more balloon-inflation side ports 136 to allow inflation and deflation of occlusion balloon 130. At distal end 126 of hollow guidewire 120, central lumen 122 of hollow guidewire 120 may be plugged or capped. Additional structures may be added to distal end 126 of hollow guidewire 120, such as a metallic coil or other flexible tubular element to assist in guiding hollow guidewire 120 through the body. Radiopaque markers and other indicia for determining the location of occlusion balloon 130 may also be added onto hollow guidewire 120.

Occlusion balloon 130 attaches near distal end 126 of hollow guidewire 120. Occlusion balloon 130 is, in one example, a spherical or cylindrical elastic membrane having proximal and distal ends affixed to an outside surface of hollow guidewire 120, such that occlusion balloon 130 may be inflated and enlarged by filling interior region 134 of occlusion balloon 130 with a fluid without leakage either through the elastic membrane material or through the attached proximal and distal ends of occlusion balloon 130. Occlusion balloon 130 may comprise, for example, one or more layers of expandable material such as polyurethane, radiopaque polyurethane material, thermoplastic polyurethane elastomers, aliphatic polyurethanes, aromatic polyurethanes, styrene-ethylene-butylene-styrene (SEBS) block copolymer, thermoplastic elastomers, low-density polyethylene, polyethylene terephthalate, polyethylene terephthalate glycol, silicone, copolymer of polyurethane and silicone, natural rubber, synthetic rubber, a thermoplastic polyamide, nylon, latex, polyethylene, polyisoprene, polyisobutylene, an elastomeric material, or combinations thereof. Attachment of occlusion balloon 130 to hollow guidewire 120 may be achieved with a suitable adhesive, heat bonds, mechanical couplers, wire wraps, bands, or other types of balloon attachment techniques. When inflation fluid 132 is injected into occlusion balloon 130, the balloon enlarges in proportion to the amount of the fluid inside. When deployed in the body, occlusion balloon 130 is enlarged to fill a region of the vessel and temporarily block flow through the vessel.

To inflate occlusion balloon 130, central lumen 122 of hollow guidewire 120 fluidly communicates with interior region 134 of occlusion balloon 130 through side port 136 in hollow guidewire 120, side port 136 being positioned between central lumen 122 and occlusion balloon 130. Side port 136 may comprise, for example, a hole, a slot, an aperture, or series of holes, slots or apertures in sidewall 162 of hollow guidewire 120 between proximal and distal ends of occlusion balloon 130. Side port 136 allows inflation fluid 132 from central lumen 122 to flow into interior region 134 of occlusion balloon 130. Inflation fluid 132 is a saline solution, a contrast fluid, or other suitable liquid that can be injected into occlusion balloon 130.

Frictional valve 140 includes core wire 142 centered within proximal end 124 of hollow guidewire 120. Core wire 142 comprises, for example, a small-diameter wire of stainless steel, nitinol, or other suitably flexible and strong material. Core wire 142 may comprise a polymeric material such as nylon or Teflon®, which has good flexibility and sealing properties yet has sufficient rigidity to controllably translate or displace core wire 142 and valve plug 150 within hollow guidewire 120.

Core wire 142 includes valve plug 150 mounted near the distal end thereof. As core wire 142 is axially translated within guidewire proximal end 124, frictional valve 140 is opened or closed, depending on the position of valve plug 150 relative to one or more inflation holes 160 formed in sidewall 162 of hollow guidewire 120. In one example, core wire 142 has proximal portion 144 extending outwardly from guidewire proximal end 124 and distal portion 146 positioned within guidewire proximal end 124. Valve plug 150 is attached to, or formed around, core wire distal portion 146, and comprises a sealing plug interference-fitted to provide a fluid seal within guidewire central lumen 122.

Valve plug 150 is formed from a polymeric material such as polyurethane, an epoxy, a silicone, or a semi-compliant polymer with good sealing and wear-resistant properties. Material for valve plug 150 may be selectively applied to an outer surface of core wire 142, dried, cured, and shaped with suitable tools to achieve the desired shape.

When valve plug 150 is positioned proximal to inflation hole 160, frictional valve 140 is open, such that inflation fluid may be injected through inflation hole 160 into central lumen 122, wherein the fluid may pass in a distal direction through hollow guidewire 120 to the interior of occlusion balloon 130. While frictional valve 140 is open, fluid may also be withdrawn through inflation hole 160 to deflate occlusion balloon 130.

Frictional valve 140 is closed when valve plug 150 is positioned across inflation hole 160, such that inflation fluid may not be injected or withdrawn through inflation hole 160. Frictional valve 140 is also closed when valve plug 150 is positioned distal to inflation hole 160, such that fluid communication is blocked between inflation hole 160 and the portion of guidewire central lumen 122 that extends distally of valve plug 150 and to occlusion balloon 130.

Core wire 142 also includes one or more frictional plugs 148 mounted on or about distal portion 146, located proximally of valve plug 150. As core wire 142 is axially translated within guidewire proximal end 124, plugs 148 move in a region between inflation hole 160 and guidewire proximal end 124. Frictional plug 148 engages guidewire inner surface 128 in a sliding interference fit. To provide a controlled friction fit against guidewire inner surface 128, frictional plug 148 may be formed from a selected plug material such as stainless steel, nitinol, polyurethane, epoxy, a silicone, a semi-compliant polymer, or other valve-compliant material.

Frictional plug 148 may also be shaped to provide a tailored valve compliance characteristic. In one example, material for frictional plug 148 is selectively applied to an outer surface of core wire 142, dried, cured, and shaped with suitable tools to achieve the desired shape. Frictional plug 148 may be short, providing a small amount of frictional resistance, or valve compliance, when core wire 142 is axially translated. In another example, frictional plug 148 is long, providing a larger amount of frictional resistance when core wire 142 is axially translated. In another example, the diameter of frictional plug 148 is selected to obtain a desired amount of friction between frictional plug 148 and guidewire inner surface 128. In yet another example, multiple frictional plugs 148 are attached along core wire 142 with predetermined lengths and spacing to control the frictional resistance. In addition, frictional plugs 148 may retain core wire 142 approximately centered within guidewire central lumen 122.

Frictional plug 148 may also reduce fluid leakage through guidewire proximal end 124 when compared to catheter-valve systems using core wire 142 without a frictional plug or to a sinusoidally shaped core wire 142. A sealing compound such as a silicone gel may be applied to core wire distal portion 146 within hollow guidewire 120 or to frictional plugs 148 to minimize the leakage of inflation fluid 132 through guidewire proximal end 124. It will be understood by one of skill in the art of occluder guidewires that having frictional plug 148 seal against leakage is often unnecessary because, after balloon 130 has been inflated, friction valve 140 is typically closed to hold balloon 130 in the inflated condition such that the inflation adapter can be removed and a treatment catheter can be slid over hollow guidewire 120. Thus, when friction valve 140 is closed and the inflation adapter has been removed, there is no fluid pressure for frictional plug 148 to seal against.

Figure 2A:
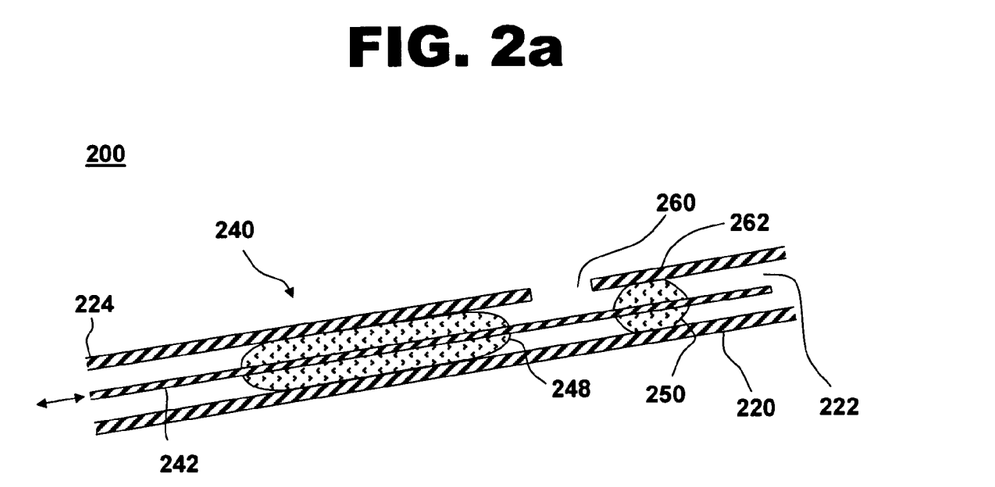
FIG. 2a and FIG. 2b show longitudinal cross-sectional views of a frictional valve for an occlusion catheter, in accordance with one embodiment of the current invention.

FIG. 2a shows a longitudinal cross-sectional view of an occlusion catheter having a frictional valve in a closed position, in accordance with one embodiment of the present invention at 200. Frictional valve 240 includes a portion of core wire 242 extending into a portion of central lumen 222 near proximal end 224 of hollow guidewire 220. Axially translating core wire 242 of frictional valve 240 controls flow of inflation fluid through central lumen 222 of hollow guidewire 220. Valve plug 250 is attached near a distal end of core wire 242 and allows inflation fluid to flow into and out of central lumen 222 of hollow guidewire 220, as described above with respect to friction valve 140. When core wire 242 is translated within hollow guidewire 220 relative to one or more inflation holes 260 formed in guidewire sidewall 262, friction valve 240 may be opened and closed, allowing fluid such as inflation fluid to be injected into and withdrawn from central lumen 222. When frictional valve 240 is closed as shown, the flow of inflation fluid is blocked, for example, to prevent air or liquid from flowing through central lumen 222 or to keep an occlusion balloon inflated while in the body. One or more frictional plugs 248 attached to core wire 242 are shaped to provide a consistent valve compliance characteristic. When valve plug 250 is positioned across or distal to inflation hole 260, frictional valve 240 is closed, as described above with respect to frictional valve 140. When valve plug 250 is positioned proximal to inflation hole 260, frictional valve 240 is open and fluid may flow through inflation hole 260 and central lumen 222 to and from a distal end of hollow guidewire 220.

Figure 2B:
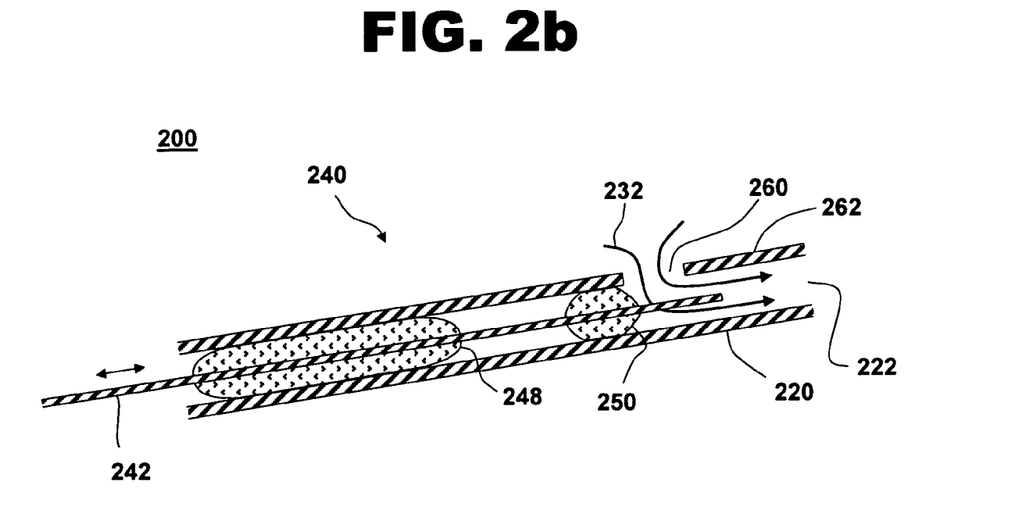

FIG. 2b shows a longitudinal cross-sectional view of the frictional valve of FIG. 2a in an open position, in accordance with one embodiment of the present invention. As core wire 242 is translated to open frictional valve 240, inflation fluid 232 may be injected through inflation hole 260 and into guidewire central lumen 222. Similarly, inflation fluid 232 may be withdrawn from guidewire central lumen 222 through open inflation hole 260.

Figure 3:
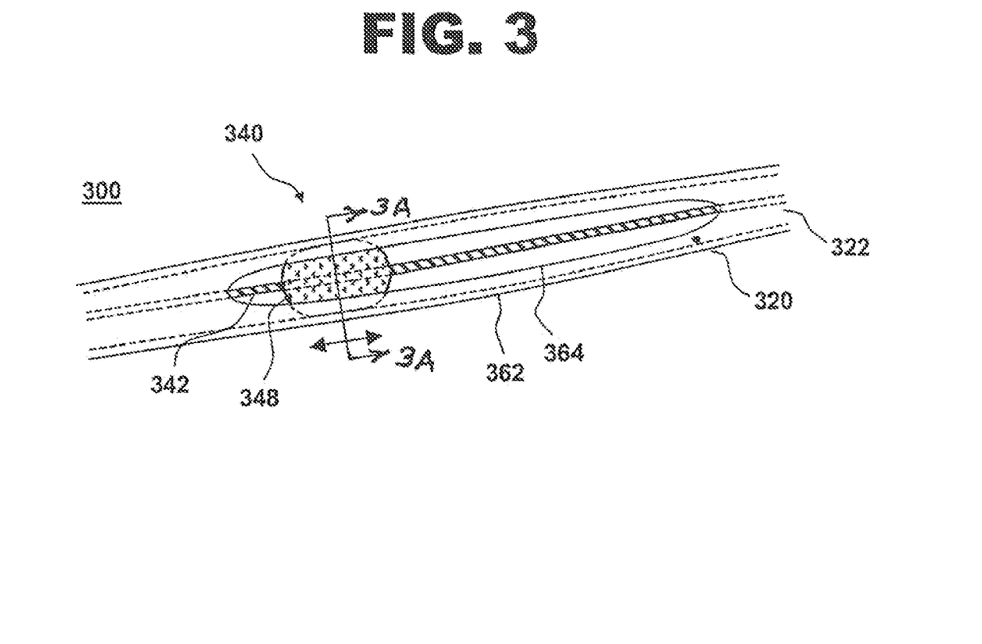
FIG. 3 shows a side view of a portion of a frictional valve including a frictional plug and a longitudinally oriented slot, in accordance with one embodiment of the current invention.
Figure 3A:
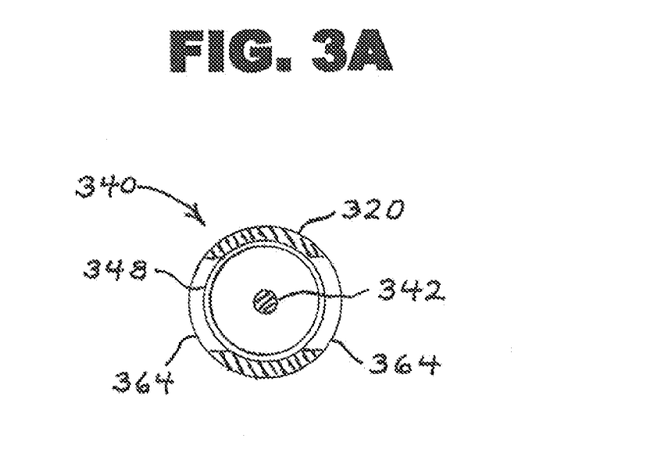
FIG. 3A shows a transverse cross-sectional view taken along line 3A-3A of the embodiment shown in FIG. 3.

FIG. 3 shows a side view of a portion of frictional valve 340 including frictional plug 348 and at least one longitudinally oriented slot 364, in accordance with one embodiment of the present invention at 300. Frictional plug 348 is attached to core wire 342. Frictional plug 348 is disposed within guidewire central lumen 322 and is positioned adjacent to longitudinally oriented slot 364 formed in guidewire sidewall 362. Frictional plug 348 and longitudinally oriented slot 364 cooperate to provide a tailored valve compliance characteristic. Inclusion of one or more longitudinally oriented slots 364 in hollow guidewire 320 reduces the valve stiffness and increases the valve compliance. As the width, length and number of longitudinally oriented slots 364 in hollow guidewire 320 increases, the valve compliance increases. The valve compliance is also dependent on the size, shape, material composition, quantity, and spacing of frictional plugs 348 attached to core wire 342. In the first illustrated embodiment of frictional valve 340, slot 364 corresponds to and functions as an inflation hole, such as inflation hole 260 discussed above. Additionally, frictional plug 348 corresponds to and functions as a valve plug, such as valve plug 250 discussed above. Therefore, the illustrated embodiment combines the functions of a frictional plug and a valve plug into a single element slidably disposed within a slotted region of a hollow guidewire.

Alternatively, a second embodiment illustrated in FIG. 3 may include a valve plug (not shown) mounted to core wire 342 distally of frictional plug 348 and operating cooperatively with an inflation hole (not shown) disposed distally of slots 364 to form a frictional valve in accordance with the invention.

Figure 4:
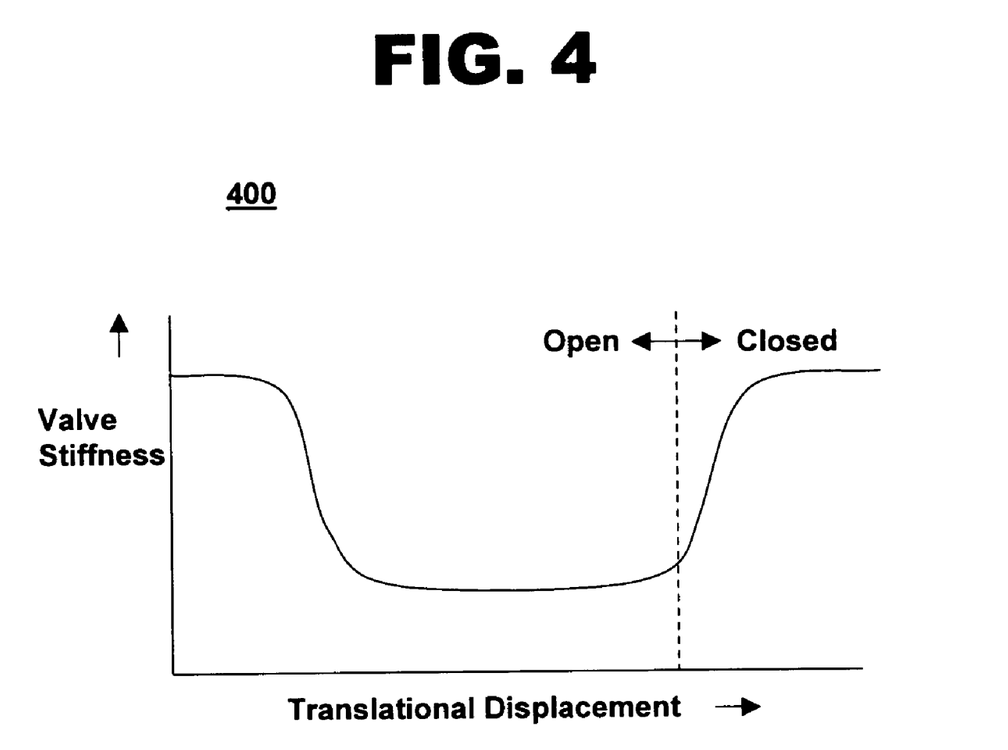
FIG. 4 is a graph of a frictional valve compliance characteristic, in accordance with one embodiment of the current invention.

FIG. 4 is a graph of a compliance characteristic for a frictional valve, in accordance with one embodiment of the present invention at 400. Valve compliance graph 400 corresponds to a frictional valve with a frictional plug adjacent to one or more longitudinally oriented slots in a hollow guidewire, such as the example shown in FIG. 3. Valve stiffness, or force required to translate core wire 342, is plotted versus the translational displacement of core wire 342, with frictional plug 348 moving along slot 364. The valve stiffness, the reciprocal of the valve compliance, is lowest when frictional plug 348 is centered along the length of longitudinally oriented slot 364 and increases as frictional plug 348 approaches the ends of slot 364. In contrast, a frictional valve without slots has a nominally constant valve stiffness or valve compliance with respect to translations of the core wire that has one or more frictional plugs. FIG. 4 shows the longitudinal transition between opening and closing the first embodiment of valve 340, wherein the functions of the frictional plug and the valve plug are combined into a single element.

In the second embodiment of FIG. 3, as frictional plug 348 moves distally with respect to longitudinally oriented slot 364, a valve plug (not shown) also mounted on core wire 342 correspondingly moves distally and covers or isolates an inflation hole (not shown) in the sidewall of hollow guidewire 320 to close the valve. Similarly, as frictional plug 348 moves proximally with respect to slot 364, the valve plug (not shown) correspondingly moves proximally and opens the inflation hole (not shown) to control the flow of fluid through the inflation hole and the central lumen of hollow guidewire 320 distal to the inflation hole and the valve plug.

The elastic properties, such as Young's modulus, of frictional plug 348 and hollow guidewire 320 affect the compliance characteristic of frictional valve 340. The quantity of longitudinally oriented slots 364, such as one, two, three, or four slots arranged around an outside surface of hollow guidewire 320, affects the value compliance characteristic. Two or more longitudinally oriented slots 364 may be formed in the wall of hollow guidewire 320 to decrease the valve stiffness and increase the valve compliance when frictional plug 348 travels through the slotted region. The shape of the longitudinally oriented slots also affects the valve compliance characteristic.

Figure 5:
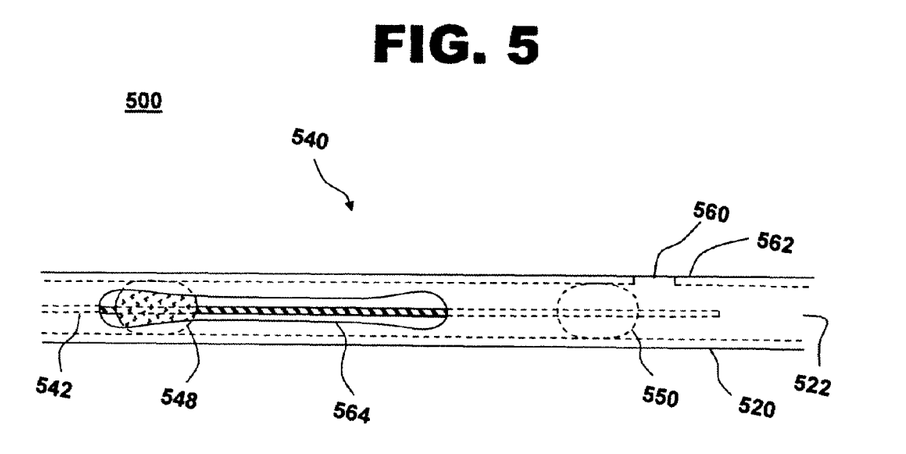
FIG. 5 shows a side view of a frictional valve with a selectively shaped longitudinally oriented slot, in accordance with one embodiment of the current invention.

FIG. 5 shows a side view of a frictional valve with a selectively shaped longitudinally oriented slot, in accordance with one embodiment of the present invention at 500. Frictional valve 540 includes hollow guidewire 520 with central lumen 522, and inflation hole 560 formed in guidewire sidewall 562. A portion of core wire 542 with valve plug 550 is positioned within a proximal end of hollow guidewire 520. Frictional plug 548 is attached to core wire 542 proximal to valve plug 550. Flow of fluid through guidewire central lumen 522 is controlled by an axial translation of core wire 542 that positions valve plug 550 with respect to inflation hole 560, while frictional plug 548 in cooperation with one or more selectively shaped longitudinally oriented slots 564 provides a tailored valve compliance characteristic.

Inclusion of longitudinally oriented slots 564 reduces the valve stiffness as core wire 542 is axially translated with frictional plug 548 adjacent to longitudinally oriented slots 564. Using a wider slot reduces the valve stiffness, whereas using a narrower slot increases the rigidity of the valve. A longer and wider slot has less stiffness than one that is shorter or narrower. A slot with wider ends and a narrower center region provides a valve compliance characteristic with less stiffness when frictional plug 548 is nearer to the ends of longitudinally oriented slot 564 than in the center. In one embodiment, hollow guidewire 520 is plastically deformed to a smaller diameter near the center of longitudinally oriented slots 564, allowing further increases of the valve stiffness when the frictional plug is near the center of the slots as compared to the stiffness when the frictional plug is at one of the ends. The variation of stiffness helps give the hand of the user a better tactile or kinesthetic indication that the valve is in one of a closed or open position as the core wire is axially displaced and the valve is opened or closed.

Figure 6:
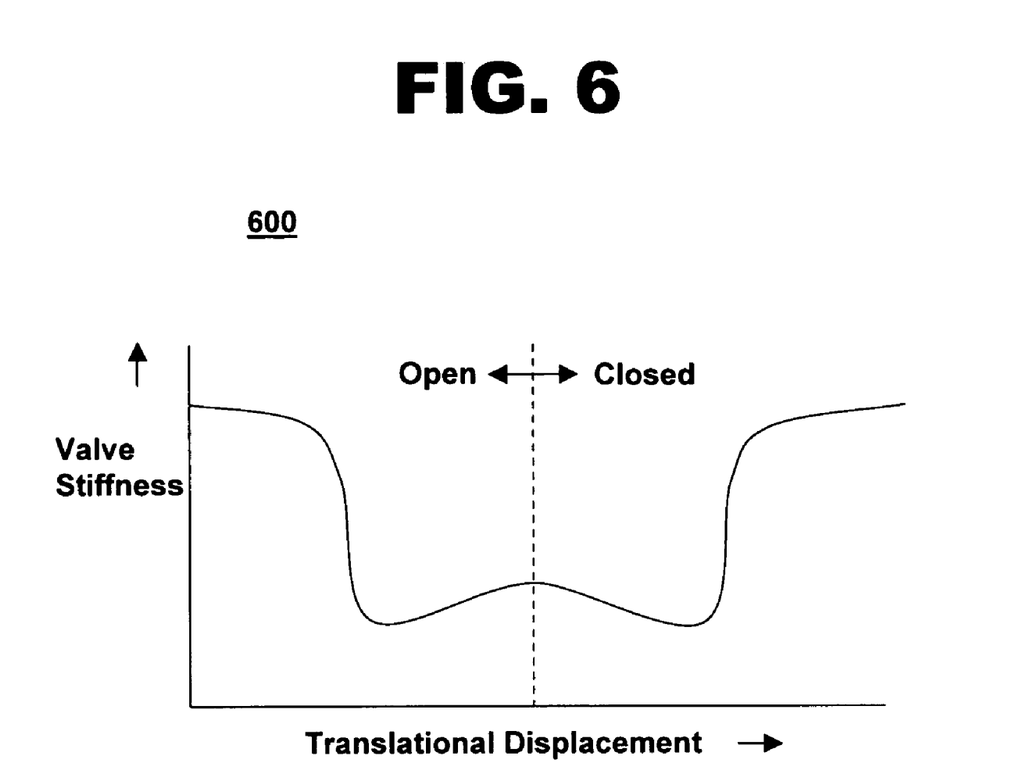
FIG. 6 is a graph of a frictional valve compliance characteristic, in accordance with another embodiment of the current invention.

FIG. 6 is a graph of a frictional valve compliance characteristic, in accordance with another embodiment of the present invention at 600. Valve compliance graph 600 illustrates the relative stiffness of a frictional valve having one or more shaped longitudinally oriented slots as described in FIG. 5. As the core wire of a frictional valve with at least one frictional plug adjacent to the slots is axially translated, the valve stiffness changes. The valve stiffness, or the reciprocal of valve compliance, is highest when the frictional plug is positioned at either end of the elongated slots or beyond, and the valve stiffness is smaller when the frictional plug is positioned within the bounds of the slots. For the valve embodiments where the slots are narrower near the center of the slots, as shown in FIG. 5, or where a hollow guidewire is inwardly deformed (not shown) near the center of the slots, the valve stiffness increases as the frictional plug is moved through the center of the slots.

FIG. 6 shows the longitudinal transition between opening and closing valve 540. The open/closed transition occurs when frictional plug 548 is approximately centered in the length of slots 564 because the spacing between valve plug 550 and frictional plug 548 is similar to the spacing between inflation hole 560 and the center of slots 564. Thus, when frictional plug 548 is positioned in the center of slots 564, valve plug 550 is positioned across inflation hole 560, causing valve 540 to be closed. Any further advancement of frictional plug 548 in a distal direction will change the associated frictional valve compliance and force valve plug 550 further into central lumen 522, further closing valve 540.

Figure 7:
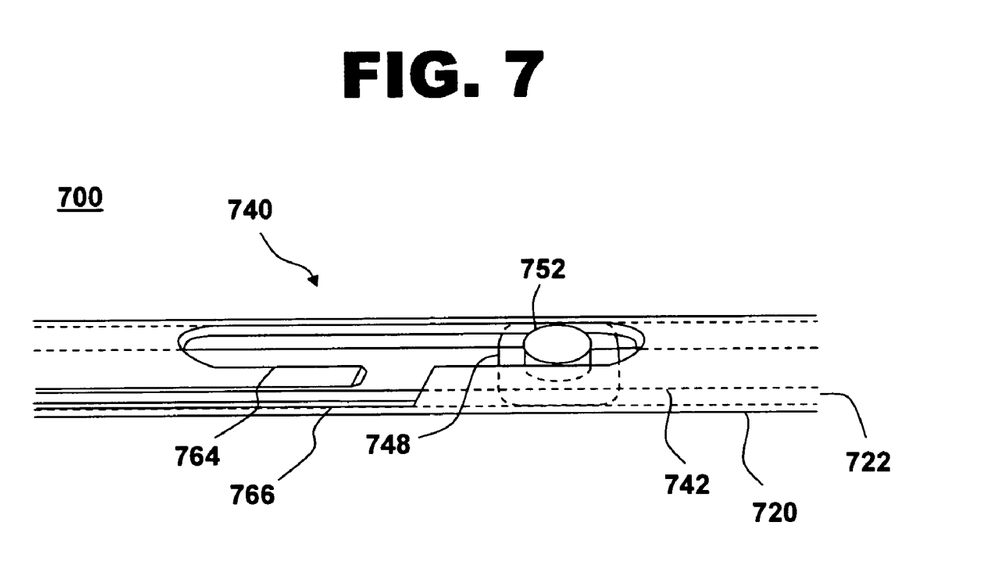
FIG. 7 shows a side view of a portion of a frictional valve, in accordance with one embodiment of the current invention.

FIG. 7 shows a side view of a portion of a frictional valve, in accordance with one embodiment of the present invention at 700. Frictional valve 740 includes frictional plug 748 and knob 752 that are attached to core wire 742. Knob 752 is positioned within a longitudinally oriented slot 764 that limits the travel of core wire 742. As core wire 742 is moved forward and backward within central lumen 722 of hollow guidewire 720, knob 752 moves freely within longitudinally oriented slot 764 until the travel is limited by one of the ends of longitudinally oriented slot 764. Frictional plug 748 can retain core wire 742 approximately centered in guidewire central lumen 722, and provides additional control of valve compliance, as discussed above with respect to frictional plugs 148, 248, 348 and 548. Additional longitudinally oriented slots 764 may be located on the opposite side of hollow guidewire 720 and around the perimeter.

Core wire 742 with knob 752 may be positioned within guidewire central lumen 722 by extending at least one longitudinally oriented slot 764 continuously to the proximal end of hollow guidewire 720. In another example, a hole is drilled through the side of core wire 742, and a short shaft is secured into the drilled hole to form knob 752. In another example, parallel slot 766 extends from a proximal end of hollow guidewire 720 to a location providing sideways, or circumferential communication with slot 764, and is included so that core wire 742 with knob 752 can be positioned within longitudinally oriented slot 764 by inserting, pushing and twisting core wire 742.

Figure 8:
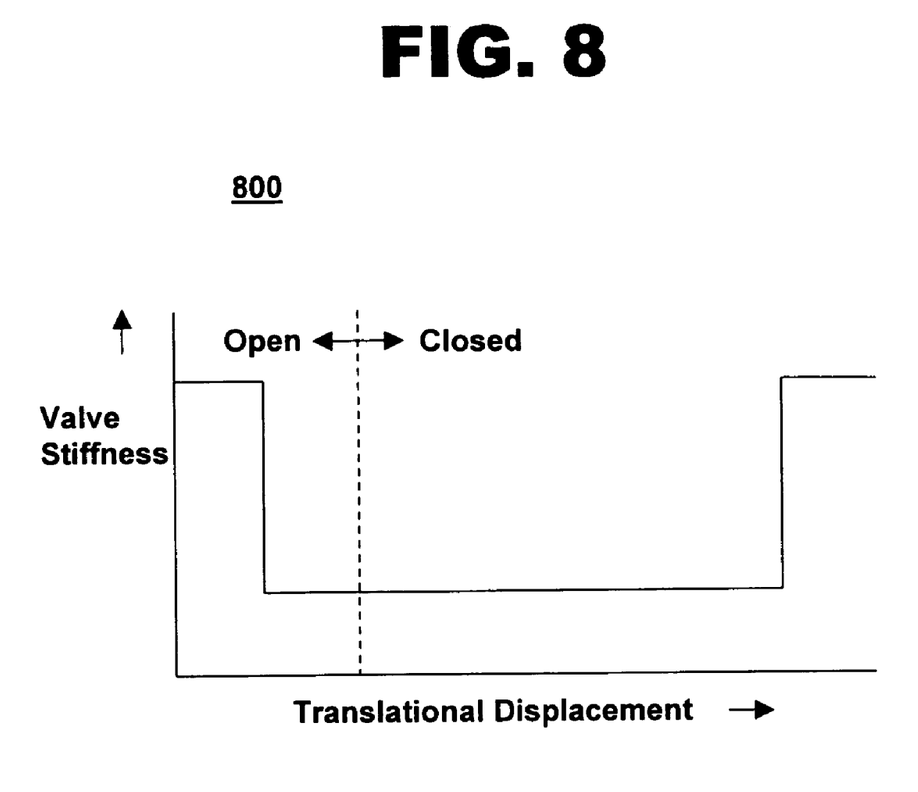
FIG. 8 is a graph of a frictional valve compliance characteristic, in accordance with another embodiment of the current invention.

FIG. 8 is a graph of a frictional valve compliance characteristic corresponding to frictional valve 740 of FIG. 7, in accordance with another embodiment of the present invention at 800. When the frictional plug is moved within the limits of the longitudinally oriented slots, the valve stiffness is relatively low, especially if frictional plug 748 has only a slight interference fit within guidewire central lumen 722.

Alternatively, frictional valve 740 may also include frictional plug 748 that has a non-interference fit within guidewire central lumen 722 and at least one frictional plug 148, 248 (not shown in FIG. 7) disposed to slide within an unslit portion of hollow guidewire 720 to provide relatively constant frictional valve compliance. At each end of the allowed travel, the valve is positioned in one of an open or a closed position. At the ends of the allowed travel, the valve stiffness increases dramatically as the frictional plug and the protruding knob is stopped against the end of the longitudinally oriented slot.

FIG. 8 shows the longitudinal transition between opening and closing valve 740. The open/closed transition occurs whenever the valve plug (not shown) is positioned across or distal to the inflation hole (not shown), causing valve 740 to be closed.

Figure 9:
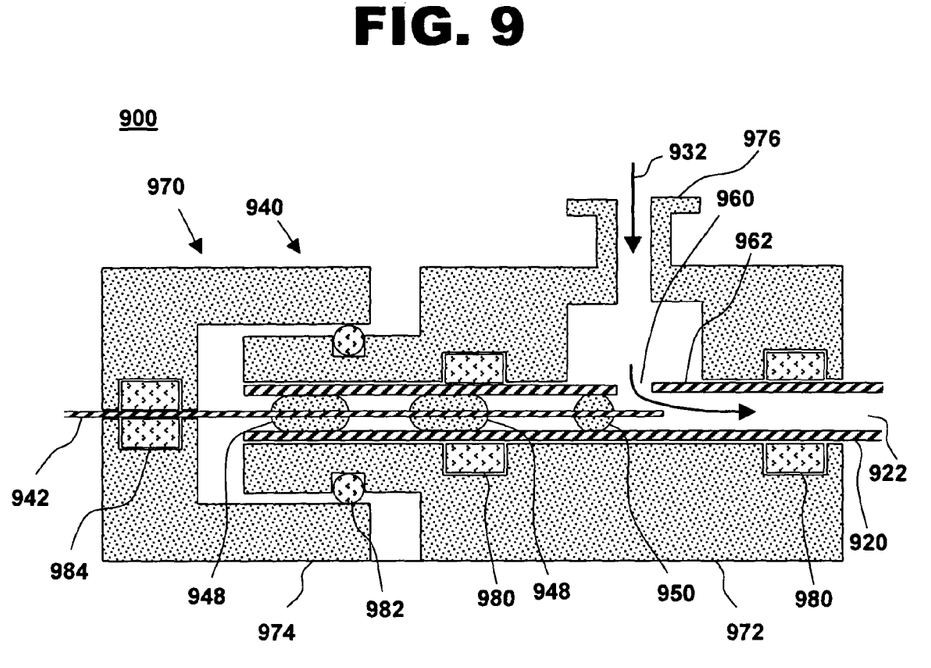
FIG. 9 shows a cross-sectional view of a detachable valve actuator for a frictional valve, in accordance with one embodiment of the current invention.

FIG. 9 shows a cross-sectional view of a detachable valve actuator for a frictional valve, in accordance with one embodiment of the present invention at 900. Valve actuator 970, when attached to frictional valve 940, translates core wire 942 to open or close frictional valve 940. Valve plug 950 is mounted adjacent the distal end of core wire 942 and cooperates with one or more inflation holes 960 in guidewire sidewall 962 to open or close frictional valve 940. At least one frictional plug 948 is attached to core wire 942 proximal to valve plug 950. Detachable valve actuator 970 is operably attached to hollow guidewire 920 and a portion of core wire 942 extending outwardly from the proximal end of hollow guidewire 920. Frictional valve 940 is translated into an open or a closed position when valve actuator 970 is actuated. As core wire 942 is translated, inflation hole 960 may be partially opened or partially closed. Valve actuator 970 may comprise first portion 972 of valve actuator 970 to grip hollow guidewire 920 and second portion 974 of valve actuator 970 to grip core wire 942 of frictional valve 940.

A series of elastomeric seals provides contact between valve actuator 970 and frictional valve 940. Seal 980 of first portion 972 of valve actuator 970 grips hollow guidewire 920 distal to inflation hole 960, securing the hollow guidewire to valve actuator 970 and preventing twisting and sliding of hollow guidewire 920 therein. Seal 984 of second portion 974 of valve actuator 970 grips core wire 942 of frictional valve 940, securing the core wire to valve actuator 970 and preventing twisting and sliding of core wire 942 therein. Optional seal 982 of valve actuator 970 is positioned between first portion 972 and second portion 974 of valve actuator 970 to prevent the leakage of fluids and to allow first portion 972 and second portion 974 of valve actuator 970 to slide with respect to one another. The seals comprise O-rings, rectangular rings, elastomeric preforms, elastomeric sealing elements, or other suitable sealing structures. The seals may have roughened surfaces to aid in gripping hollow guidewire 920 and core wire 942. When valve actuator 970 is attached to frictional valve 940, core wire 942 is translated when valve actuator second portion 974 is translated with respect to valve actuator first portion 972.

An inflation fluid supply may be connected to inflation fluid port 976, which may comprise, for example, a Luer fitting operably coupled to valve actuator 970. When frictional valve 940 is open, inflation fluid 932 can enter inflation fluid port 976 to flow through inflation hole 960 and into guidewire central lumen 922.

Various grooves, guides and feed mechanisms (not shown) can allow core wire 942 and hollow guidewire 920 to be placed readily and accurately into valve actuator 970. Latches may be used, for example, to close and secure valve actuator 970 onto core wire 942 and hollow guidewire 920 when core wire 942 and hollow guidewire 920 are positioned correctly. In other versions of valve actuator 970, core wire 942 and hollow guidewire 920 may be fed into one end of valve actuator 970 until positioned appropriately to actuate frictional valve 940.

Other mechanisms, such as clamps, tensioners and knobs, can be coupled to valve actuator 970 to aid in the compression of elastomeric seals against the outside surface of hollow guidewire 920 and core wire 942 of frictional valve 940.

Indexing mechanisms and stops may be added to aid in accurate, repeatable translation of the core wire to open and close the frictional valve. The reliable and repeatable frictional valve compliance characteristics provided by various embodiments of the inventive frictional valve contribute to the precision of such indexing mechanisms. Even after repeated opening and closing of the frictional valve, the clinician can still expect the balloon to remain inflated when the mechanism indicates that the valve is closed. Similarly, the clinician can expect the balloon to be inflatable or deflatable when the mechanism indicates that the valve is open.

Figure 10:
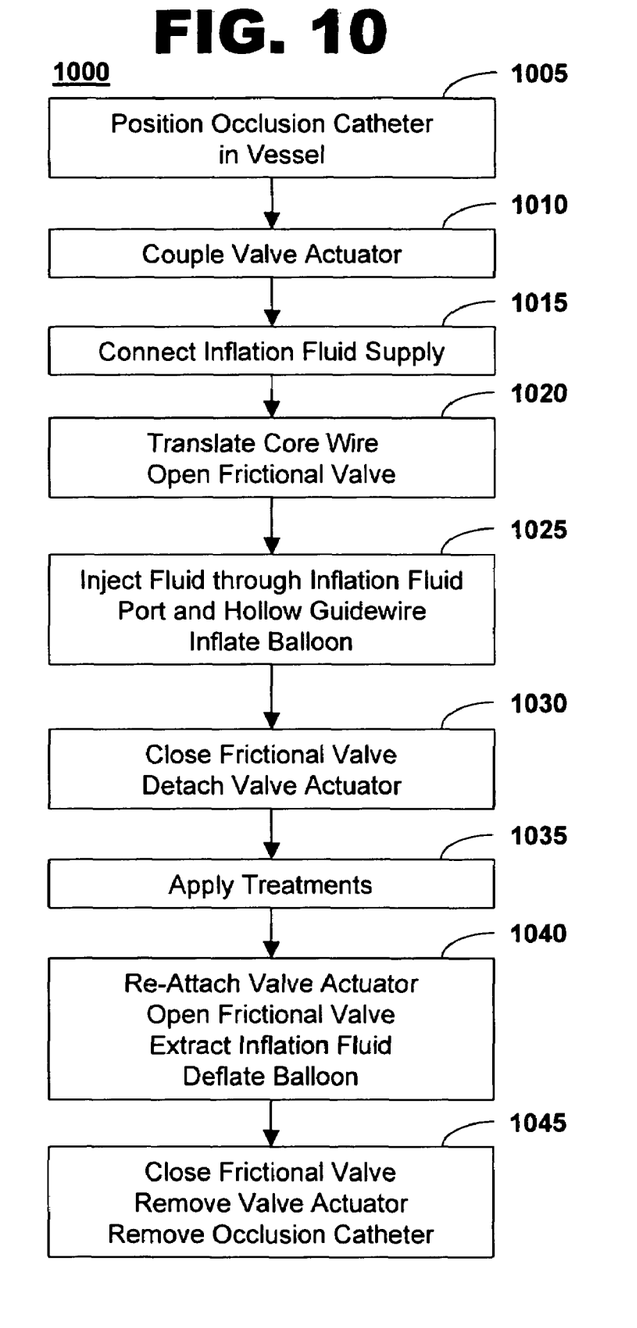
FIG. 10 is a flow diagram of a method of treating a vascular condition, in accordance with one embodiment of the current invention.

FIG. 10 is a flow diagram of a method for treating a vascular condition, in accordance with one embodiment of the present invention at 1000. Vascular condition treatment method 1000 includes various steps to inflate and deflate an occlusion balloon near the distal end of an occlusion catheter using a frictional valve, and to provide one or more vascular treatments for the prevention or correction of various ailments and deficiencies including those associated with the cardiovascular system, the cerebrovascular system, urogenital systems, biliary conduits, abdominal passageways and other biological vessels within the body.

An occlusion catheter with a frictional valve is positioned in a vessel, as seen at block 1005. The hollow guidewire with the occlusion or dilation balloon at the distal end is manipulated manually through the vascular system to the desired location for placement of the balloon. For example, a needle puncture is made in the body near the femoral artery, and the hollow guidewire with the occlusion balloon is inserted through the puncture, through the femoral artery, and into a position within a blood vessel where the balloon is to be inflated. A central lumen with the hollow guidewire and other lumens may be purged with inflation fluid such as diluted contrast fluid or saline solution before the occlusion catheter is inserted into the body. Prior to the positioning of the occlusion catheter, fluoroscopic contrast fluid may be injected into the blood vessel in order to identify, visualize and verify the location of a stenosis, blockage, or other medical condition within the blood vessel.

A detachable valve actuator is coupled to the core wire of the frictional valve and to the hollow guidewire, as seen at block 1010. The valve actuator is coupled to a portion of the core wire extending outwardly from the proximal end of the hollow guidewire. Depending on the style of valve actuator, the core wire and the hollow guidewire may be fed through the valve actuator, or sandwiched between two portions of the valve actuator by closing a lid or other coupling mechanism. When an inflation hole in a sidewall of the hollow guidewire is placed correctly within the valve actuator, the valve actuator is secured to the hollow guidewire and to the core wire of the frictional valve.

At this point, an inflation fluid supply is connected to the valve actuator, as seen at block 1015. Inflation fluid such as dilute contrast agent or other suitable fluid may be stored in an inflation device and connected to an inflation fluid port, such as a Luer fitting, on the valve actuator. Various standard procedures can be used to remove air and other gases from the inflation device, lines connected to the valve actuator, and to chambers within the valve actuator.

The core wire of the frictional valve is axially translated, as seen at block 1020. The valve plug is positioned relative to an inflation hole formed in the sidewall of the hollow guidewire. When the core wire is translated within the central lumen of the hollow guidewire, a portion of the core wire extending within the hollow guidewire is translated such that the valve plug is positioned proximally to the inflation hole in the sidewall of the hollow guidewire. With the frictional valve and the inflation hole thus opened, inflation fluid can flow through the valve. Translations of the core wire may be limited, for example, by one or more frictional plugs attached to the core wire at a position proximal to the valve plug. The frictional plugs may center the core wire within the hollow guidewire during axial translation. The frictional plugs control an axial compliance of the wire within the hollow guidewire, the axial compliance being a contributor to the overall valve compliance characteristic.

One or more selectively shaped longitudinally oriented slots may be formed in the hollow guidewire, with the frictional plugs positioned adjacent to the slots. As the core wire and frictional plugs are axially translated within the hollow guidewire, slotted regions adjacent to the frictional plugs are radially expanded and contracted, providing precise control over the valve compliance characteristic. Additional control over the valve compliance characteristic may be provided, for example, by selectively shaping the frictional plugs or the longitudinally oriented slots, or by mechanically deforming the hollow guidewire inwardly in the vicinity of the slots during manufacture.

Inflation fluid is injected through the inflation fluid port, through the open inflation hole and into the central lumen within the hollow guidewire, as seen at block 1025. The occlusion balloon near the distal end of the hollow guidewire and in communication with the hollow guidewire is inflated with fluid traversing one or more balloon-inflation side ports between the central lumen within the hollow guidewire and an interior region of the occlusion balloon. The occlusion balloon is inflated with the injected inflation fluid to the desired size, the size and position of the balloon being monitored, for example, with injections of radiopaque contrast fluid and associated x-ray imaging systems.

When the balloon is inflated to the desired size, the frictional valve is closed, as seen at block 1030. A translational movement or displacement of the core wire closes the frictional valve, preventing inflation fluid from flowing through the inflation hole, and keeping the balloon inflated. The valve actuator may be detached and removed.

When the valve actuator has been removed, various treatments can be applied to the vessel, as seen at block 1035. For example, a stent-delivery catheter may be inserted over the hollow guidewire and into position within the body prior to deployment of a stent. Other catheters such as an aspiration catheter or an imaging catheter can be positioned over the hollow guidewire and moved into place.

When the treatments have been completed, the valve actuator is reattached, as seen at block 1040. Axially translating a core wire of the frictional valve opens the frictional valve, allowing fluid to flow through the inflation hole. Inflation fluid is extracted, and the occlusion balloon deflates. Inflation fluid within the balloon flows through the balloon inflation holes into the central lumen of the hollow guidewire, through the central lumen, through the inflation holes near the proximal end of the hollow guidewire, and out through the inflation fluid port in the valve actuator until the balloon deflates. Inflation fluid may be extracted, for example, with an inflation/deflation device, with negative pressure, or by elastic restoring forces within the balloon.

The frictional valve is closed by axially translating the core wire of the frictional valve to close the inflation hole, as seen at block 1045. The valve actuator is removed from the hollow guidewire and the core wire, and then the hollow guidewire with the occlusion balloon are removed from the body.

Variations and alterations in the design, manufacture and use of the occlusion catheter and the frictional valve are apparent to one skilled in the art, and may be made without departing from the spirit and scope of the present invention. While the embodiments of the invention disclosed herein are presently considered to be preferred, various changes and modifications can be made without departing from the spirit and scope of the invention. The scope of the invention is indicated in the appended claims, and all changes that come within the meaning and range of equivalents are intended to be embraced therein.

What is claimed is:

1. A system for treating a vascular condition, comprising:
a hollow guidewire having a central lumen and an inflation hole formed in a sidewall of a proximal end of the hollow guidewire, wherein a portion of the hollow guidewire further comprises at least one longitudinally oriented slot formed therein;
an occlusion balloon attached proximate to a distal end of the hollow guidewire; and
a frictional valve, wherein the frictional valve includes a distal portion of a core wire positioned within the proximal end of the hollow guidewire and a valve plug attached to the distal portion of the core wire and at least one frictional plug attached to the core wire proximal to the valve plug, the at least one frictional plug positioned adjacent to the at least one longitudinally oriented slot; wherein a flow of a fluid through the central lumen of the hollow guidewire is controlled by axial translation of the core wire to position the valve plug with respect to the inflation hole, while the frictional plug provides a tailored valve compliance characteristic.

2. The system of claim 1 wherein the frictional plug is shaped to provide the tailored valve compliance characteristic.

3. The system of claim 1 wherein the frictional plug comprises a plug material selected from the group consisting of stainless steel, nitinol, polyurethane, an epoxy, a silicone, and a semi-compliant polymer.

4. The system of claim 1 wherein the frictional plug reduces leakage of the fluid through the proximal end of the hollow guidewire.

5. The system of claim 1 wherein the frictional plug centers the core wire within the central lumen of the hollow guidewire.

6. The system of claim 1 wherein a quantity of the at least one longitudinally oriented slot provides the tailored valve compliance characteristic.

7. The system of claim 1 wherein a shape of the at least one longitudinally oriented slot provides variation to the tailored valve compliance characteristic along the slot.

8. A frictional valve for an occlusion catheter, comprising:
a hollow guidewire having a central lumen and an inflation hole formed in a sidewall of a proximal end of the hollow guidewire, wherein a portion of the hollow guidewire further comprises at least one longitudinally oriented slot formed therein;
a distal portion of a core wire positioned within the proximal end of the hollow guidewire;
a valve plug attached to the distal portion of the core wire; and
at least one frictional plug attached to the core wire proximal to the valve plug, the at least one frictional plug positioned adjacent to the at least one longitudinally oriented slot, wherein a flow of a fluid through the central lumen of the hollow guidewire is controlled by axial translation of the core wire to position the valve plug with respect to the inflation hole, while the frictional plug provides a tailored valve compliance characteristic.

9. The valve of claim 8 wherein the frictional plug is shaped to provide the tailored valve compliance characteristic.

10. The valve of claim 8 wherein the frictional plug comprises a plug material selected from the group consisting of stainless steel, nitinol, polyurethane, an epoxy, a silicone, and a semi-compliant polymer.

11. The valve of claim 8 wherein the frictional plug reduces fluid leakage through a proximal end of the hollow guidewire.

12. The valve of claim 8 wherein the frictional plug centers the core wire within the central lumen of the hollow guidewire.

13. The valve of claim 8 wherein a quantity of the at least one longitudinally oriented slot provides the tailored valve compliance characteristic.

14. The valve of claim 8 wherein a shape of the at least one longitudinally oriented slot provides a variation to the tailored valve compliance characteristic along the slot.

* * * * *